United States Patent [19]
Li et al.

[11] Patent Number: 5,854,063
[45] Date of Patent: Dec. 29, 1998

[54] METHOD AND APPARATUS FOR SPECTROPHOTOMETRIC OBSERVATION OF PLANTS

[75] Inventors: Ning Li; Larry S. Daley, both of Corvallis, Oreg.

[73] Assignee: The State of Oregon Acting by and through the State Board of Higher Education on Behalf of Oregon State University, Corvallis, Oreg.

[21] Appl. No.: 739,380

[22] Filed: Oct. 29, 1996

Related U.S. Application Data

[60] Provisional application No. 60/010,025 Jan. 16, 1996.
[51] Int. Cl.$^6$ .................................. G01J 3/30; G01J 3/42; C12M 1/00; G01N 21/00
[52] U.S. Cl. ............................... 435/287.1; 435/283.1; 356/72; 356/73; 356/317; 356/318; 356/319; 356/432; 356/435
[58] Field of Search ...................... 435/283.1, 287.1; 424/9.1; 356/317, 318, 319, 432, 435, 72, 73

[56] References Cited

U.S. PATENT DOCUMENTS

| | | | |
|---|---|---|---|
| 4,224,304 | 9/1980 | Sawai et al. | 424/12 |
| 4,407,008 | 9/1983 | Schmidt et al. | 358/93 |
| 4,650,336 | 3/1987 | Moll | 356/317 |
| 5,130,545 | 7/1992 | Lussier | 250/459.1 |
| 5,238,171 | 8/1993 | Takabayashi et al. | 250/205 |
| 5,329,352 | 7/1994 | Jacobsen | 356/301 |
| 5,337,139 | 8/1994 | Shirasawa | 356/73 |
| 5,381,224 | 1/1995 | Dixon et al. | 356/72 |
| 5,469,251 | 11/1995 | Kosaka et al. | 356/73 |
| 5,658,418 | 8/1997 | Coronel et al. | 156/345 |

FOREIGN PATENT DOCUMENTS

| | | | |
|---|---|---|---|
| 33 03 510 | 7/1983 | Germany | 250/458.1 |
| 87/06698 | 11/1987 | WIPO | 250/458.1 |

OTHER PUBLICATIONS

Francine Heisel, et al., "Detection of Nutrient Deficiencies of Maize by Laser Induced Fluorescence Imaging," *J. Plant Physiol.*, vol. 148, pp. 622–631 (1996).

Katharina Siebke, et al., "Assimilation images of leaves of *Glechoma hederacea*: Analysis of non–synchronous stomata related oscillations," *Planta*, vol. 196, pp. 155–165 (1995).

Bernard Genty[AB], et al., "Quantitative Mapping of Leaf Photosynthesis using Chlorophyll Fluorescence Imaging," *Aust. J. Plant Physiol.*, vol. 22, pp. 277–284 (1994).

H. K. Lichtenthaler, et al., "Detection of Vegetation Stress Via a New High Resolution Fluorescence Imaging System," *J. Plant Physiol.*, vol. 148, pp. 599–612 (1996).

James M. Fenton, et al., "Computer aided fluorescence imaging of photosynthesis systems: *Application of video imaging to the study of fluorescence induction in green plants and photosynthetic bacteria*," *Photosynthesis Research*, vol. 26, pp. 59–66 (1990).

Patrice Benoit, et al., "New Instruments for Remote Sensing of Plant Stress," *Photosynthesis: from Light to Biosphere*, vol. 4, pp. 757–760 (1995).

Li Ning, et al., "Construction of an Imaging Visible Spectrophotometer and Its Application to Plant Sciences," *Spectroscopy* 9(7), Sep. 1994, pp. 41–48.

Omasa et al. Plant Physiol. vol. 48, pp. 748–752, 1987.

Daley, P. F. Canadian J. Plant Pathol. vol. 17 (2), pp. 167–173, 1995.

*Primary Examiner*—Leon B. Lankford, Jr.
*Assistant Examiner*—Christopher R. Tate
*Attorney, Agent, or Firm*—Klarquist Sparkman Campbell Leigh & Whinston, LLP

[57] ABSTRACT

An instrument is described for making both fluorometric and spectrophotometric images of plants. The instrument includes two sources of electromagnetic radiation, optical components to direct the radiation, excitation and emission filters, and an imaging device. The instrument can be used to produce high resolution spectrophotometric images of living plants by correcting for water path length.

7 Claims, 2 Drawing Sheets

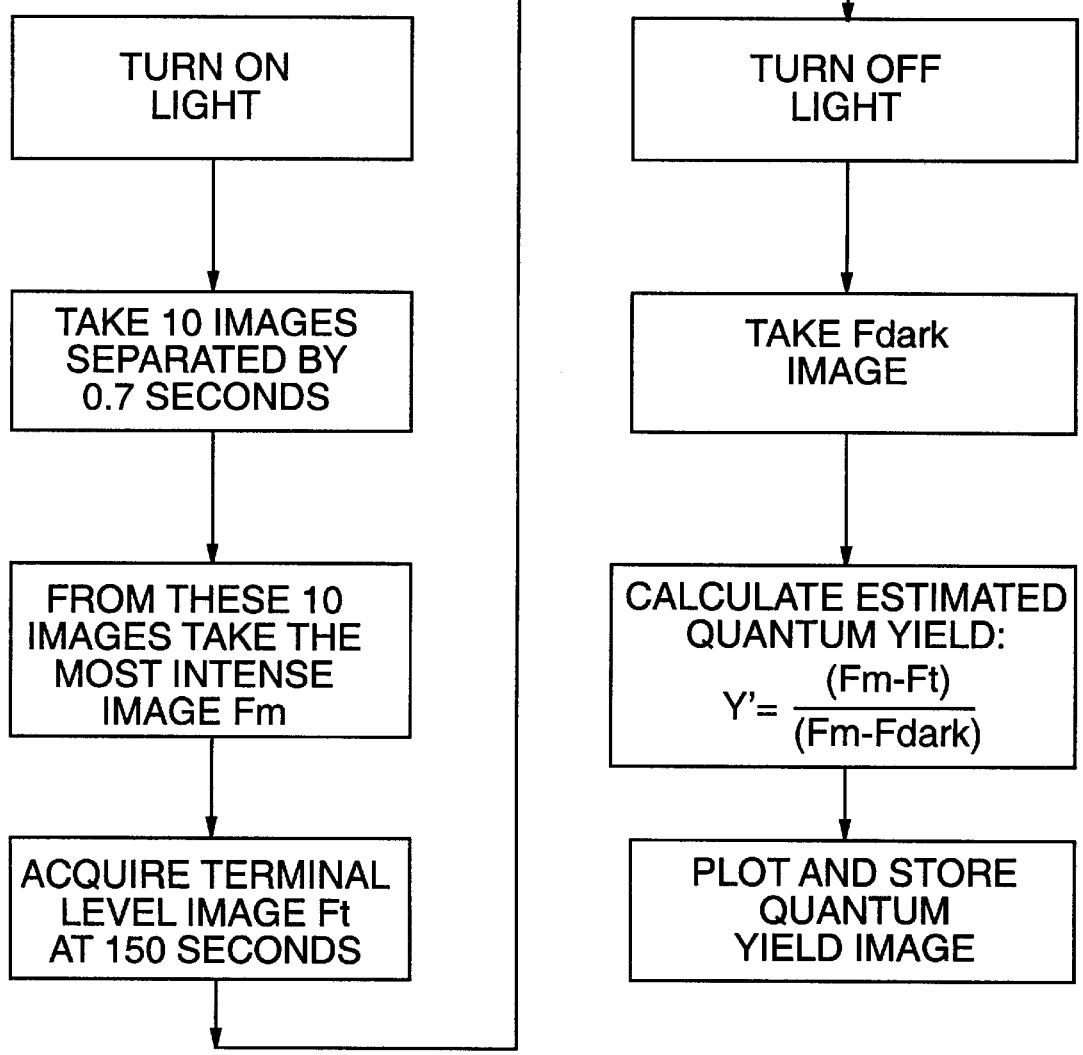

METHOD AND APPARATUS FOR SPECTROPHOTOMETRIC OBSERVATION OF PLANTS

This application claims the benefit of U.S. provisional application No. 60/010,025, filed Jan. 12, 1996.

TECHNICAL FIELD

This invention relates to the measurement and analysis of light emitted or transmitted by plant materials.

BACKGROUND OF THE INVENTION

Instruments have been developed for absorbance-based spectroscopy of plant tissues, for example, as described in Ning, et al., "Construction of an Imaging Visible Spectrophotometer and Its Application to Plant Sciences", *Spectroscopy* 9 (7), 41–48 (1994). These devices have proved useful to recording leaf spectra over 2-D space. It has been suggested that such imaging spectroscopes will be useful to measure plant physiology parameters and histochemical change.

Such devices have not been well suited for rapid screening of living plants, however, due to the length of time required to make a spectroscopic observation. And, such devices have not been useful for quantifying the amount of water in a living plant tissue specimen. Thus, there remains a need for a more versatile instrument which can both screen plants rapidly and make more detailed spectroscopic observations by correcting for water path length of a living plant sample.

SUMMARY OF THE INVENTION

A method and apparatus for more efficiently studying plant samples has now been discovered. The instrument includes a CCD camera for receiving electromagnetic radiation from a plant sample and two sources of electromagnetic radiation. The first source directs radiation towards the surface of a plant sample which faces the CCD camera and provides radiation of a wavelength suitable to excite fluorescence from photosynthetic components of the plant sample. The second radiation source directs radiation toward the sample surface opposite the CCD camera so that the CCD camera receives radiation transmitted by the plant sample. A computer receives data from the CCD camera and computes an effective quantum yield for photosynthetic efficiency based on the fluorescence data and computes spectrometric data from observations of transmitted light. A switching mechanism is provided to alternate between illumination with the first radiation source and the second radiation source so that the instrument can alternatively act as a fluorometer and as a spectrophotometer without moving a plant sample from a predetermined location relative to the CCD camera.

In a useful operating procedure to detect plant abnormalities, a plant sample is positioned at the predetermined location and its fluorescence observed by the CCD camera. If the fluorometric data does not indicate any abnormality in the plant sample, a second plant sample is placed at the predetermined location and the fluorometric observation repeated. If, however, the fluorometer detects that a plant sample or a portion of a plant sample is abnormal in some regard, illumination by the first radiation source is ceased and illumination by the second radiation source is commenced so that a spectrophotometric study of the plant is made to better characterize the nature of the abnormality. In this way, a large number of plants can be screened rapidly by fluorometry while use of the slower spectrophotometric analysis can be reserved for use only with plants for which some abnormality has been detected. A transport mechanism may be used to automatically move plants into position or to move the instrument from plant to plant.

Quantitative data concerning the water content of a plant sample can be calculated by measuring the degree to which light is attenuated when the instrument is used in a spectrographic mode. This is accomplished rapidly since the path length of living plant tissue can be determined in advance by the method described herein. Path length information can also be used to normalize spectrographic data to produce spectrophotometric images of greater clarity.

BRIEF DESCRIPTION OF THE DRAWINGS

In order that the invention may be clearly understood, it will now be described, by way of examples, with reference to the following figures:

FIG. 3 is a flow chart showing a preferred protocol for measuring the estimated quantum yield, C,DD'.

DETAILED DESCRIPTION

According to the present invention, a single instrument can be used for both fluorometric and spectrophotometric observation of living plant tissue. Automatic correction for Rayleigh scattering and water path produce highly useful images.

Apparatus

Figure 1:
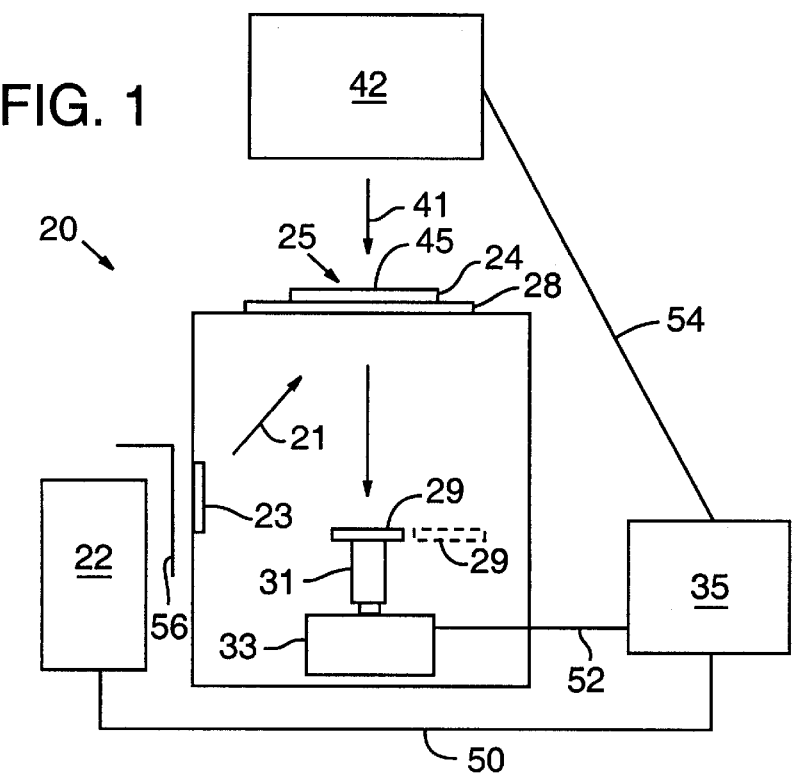
FIG. 1 is a schematic view of an instrument according to the present invention.

FIG. 1 shows an instrument 20 which serves both as an imaging fluorometer and an imaging spectrophotometer. The instrument includes two sources of electromagnetic radiation, optical components to direct the radiation, excitation and emission filters, an imaging device, and a digital computer. In this embodiment, radiation 21 from a first source 22 is used to illuminate (or excite) a sample of plant material, such as a leaf sample 24. Incident light from this source is filtered by an excitation filter 23 and impinges on the leaf sample 24 which is positioned at a predetermined location 25 behind a sample window 28. The light excites fluorescence from the sample 24; this emitted fluorescence passes through an emission filter 29 and lens 31 on its way to an imaging device 33. The collected image is then sent to a digital computer 35 for analysis.

Figure 2:
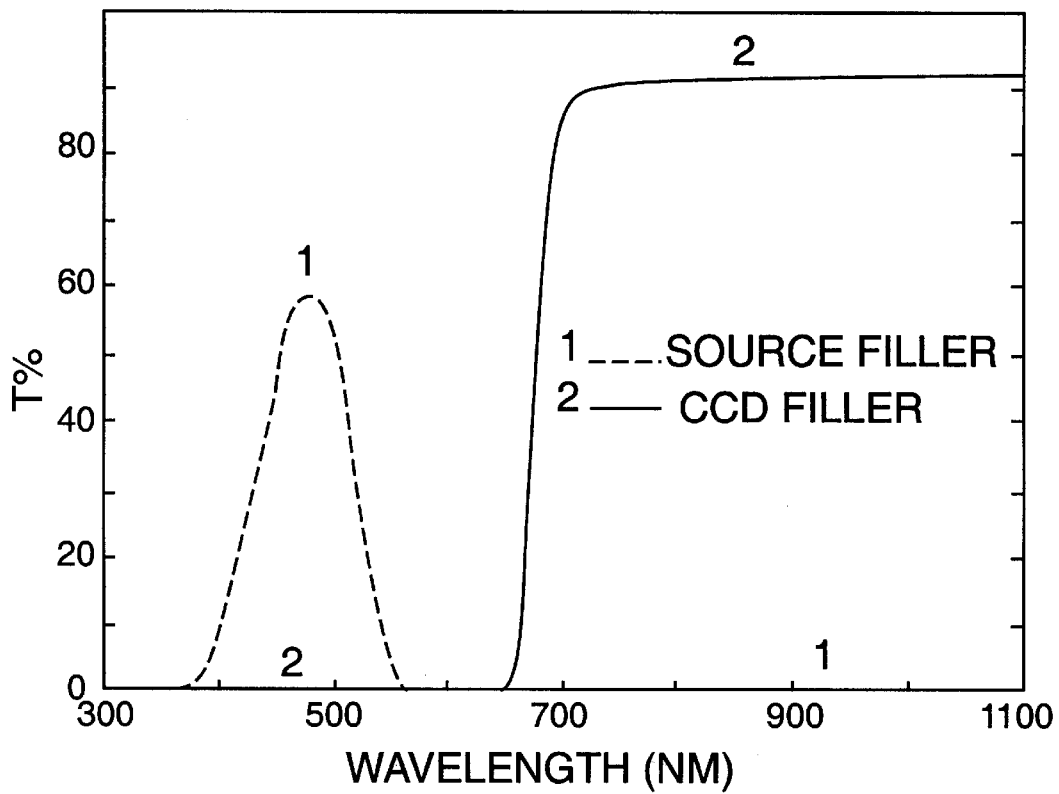
FIG. 2 is a plot of percent transmission versus wavelength for excitation and emission filters used in the instrument for imaging fluorometry.

The radiation source 22 emits light of a wavelength suitable for exciting fluorescence from photosynthetic systems. An example is a 500 W, 120-volt projector lamp (model CZX/DAD, GTE Products Inc., Winchester, Ky.) in combination with one or more filters to eliminate undesired light. The spectral properties of two suitable filters are shown in FIG. 2 and are further described in Ning, et al., "Imaging Fluorometer to Detect Pathological and Physiological Change in Plants," *Applied Spectroscopy*, October 1995, which is incorporated herein by reference. On the excitation side, the excitation filter 23 transmits light with wavelengths suited to exciting fluorescence from photosynthetic components. On the emission side, the emission filter 29 blocks the shorter-wavelength scattered excitation light and passes the longer-wavelength fluorescence.

Radiation 41 from a second radiation source 42 is used to measure attenuation by the sample 24. A monochromatic light beam 41 impinges on the back surface 45 of the leaf sample 24. A portion of light 41 passes through the sample 24 and lens 31 on its way to an imaging device 33. When making spectroscopic observations, the filter 29 is moved to a position, indicated by broken lines in FIG. 1, that is out of the light path to the imaging device 33. The collected image data is then sent to a digital computer 35 for analysis.

The radiation source 42 includes a light source, such a 500 W, 120-volt projector lamp (model CZX/DAD, GTE Products Inc., Winchester, Ky.) and a tunable monochromator, such as a Jarrell-Ash single monochromator, model 82-410 (Scientific Measurement Systems, Grand Junction, Colo.) driven by a step motor (HY 200, Oregon Microsystems, Beaverton, Oreg.). Other devices, such as optical acoustical filters and liquid crystal filters should work as substitutes. The radiation source 42 is used to produce monochromatic light 41 at wavelengths suitable for spectral imaging of the sample 24.

Image data are collected by the imaging device 33, which is a charge-coupled device (CCD) camera. A CCD camera is preferred because of its sensitivity and its highly linear response to illumination intensity. An example is a thermoelectrically cooled 12-bit CCD camera (Lynxx PC, CCD Digital Imaging System, Spectra-Source Instruments, Westlake Village, Calif.) with a spatial resolution of 165 by 192 (31,680) pixels.

The digital computer 35 is connected to the first radiation source 22, imaging device 33, and the second radiation source 42 through interface boards and cables 50, 52, 54. The computer 35 thereby controls the operation of the radiation sources and imaging device. The computer is programmed to turn the radiation sources 22, 42 on and off at appropriate times, for example by operation shutters such as the shutter 56 shown in FIG. 1. The computer can also be used to automatically control positioning of the filter 29.

Suitable results can be obtained using an IBM/PC compatible computer (e.g. containing a Pentium processor, 90 MHz, Intel Corp., Palo Alto, Calif.) connected to the CCD camera through a PC interface board (Lynxx PC, Spectra-Source Instruments). Data acquisition speed and number of data points are enhanced by using a fastest available computer.

Storage of digital images requires considerable system memory. Images may be stored on a hard disk or on removable tapes or cartridges. An example of a suitable storage system is a removable 88 MByte SyQuest cartridge (Model SQ800) on the corresponding internal drive (SyQuest Technology, Fremont, Calif.) for easy access.

Communication with the camera and data analysis may be accomplished using programs developed with suitable software. For example, communication with the camera may be accomplished using a program written in Borland C++3.1 (Borland's International, Scotts Valley Calif. 95067). Data may be retrieved and processed using a numerical software package called MATLAB (The MathWorks, Inc., Natick, Mass.).

Fluorometric Image Acquisition

The imaging fluorometer captures an image of the fluorescence emitted by an illuminated sample containing photosynthetic components. Exposure and total acquisition times depend on the sample and imaging device. For a plant leaf and CCD camera, exposure times are typically about 0.1 s; complete digitization and storage of one image typically takes about 0.6 s using an IBM/PC compatible computer having a 90 MHz Pentium chip. Shorter times can be achieved by using computers with faster processors.

For some applications, a series of images is required, each collected at a defined time. Such acquisition is readily accomplished if the imaging fluorometer is under the control of a digital computer.

Images obtained at different times may be analyzed individually, or combined to yield images of the effective quantum yield. The effective quantum yield is an empirical estimate of the quantum yield based on several improvements to the standard quantum yield equation First, the need to measure $F_o$, which occurs on the picosecond time scale, is circumvented by replacing $F_o$ with $F_t$. This approximation is generally valid, with some important exceptions, as noted below. Second, the need to obtain an image at the precise time corresponding to $F_p$ is circumvented by obtaining images at a series of times and then approximating $F_p$ by the maximum value $F_m$ obtained in the series. This approximation enables the fluorometer flexibly to handle differences in timing that reflect differences in species, physiology, and pathology. Finally, fluorescence values are corrected, pixel by pixel, for errors introduced by the imaging device. An especially simple correction is to subtract from all fluorescence values the dark signal, $F_{dark}$, obtained in the absence of illumination, although other corrections may also be used.

Combining these three improvements gives an empirical estimate of the quantum yield, denoted Y':

$$Y' \cong (F_m - F_t)/(F_m - F_{dark}) \tag{1}$$

The dark current is not shown in the numerator of equation (1) because it cancels out of the difference. Correcting for the dark signal always increases the value of Y', because it always decreases the denominator in Eq. 2.

As a practical matter, the three variables in equation (1) are easily measured for each pixel. $F_m$ is defined as the maximum value of the fluorescence obtained from about the first 10 images. $F_t$ is defined as the value of the fluorescence after about 150 seconds, by which time steady-state has been reached. Finally, $F_{dark}$ is defined as the value of the dark signal obtained in the absence of illumination. An image of quantum yield can then be generated by calculating Y' on a pixel-by-pixel basis, using associated values of $F_m$, $F_t$, and $F_{dark}$. A flow chart showing a preferred protocol for calculating Y' is shown in FIG. 3.

Although in this described use the time of $F_m$ is determined for the total leaf image, and not on a pixel-by-pixel basis, the value at that time for each pixel becomes the $F_m$ used in the estimation of Y'. However, since the data set can be considered as in a three dimensional matrix of space and time in the MATLAB program, a variant program was run which calculated time of $F_m$ for each pixel was tested and found to generate equivalent images in healthy leaves.

Values of Y' are typically 0.75–0.85 for healthy dark-adapted leaves; lower values indicate reduced efficiency of energy transfer to the RC or else damaged RC.

Examples of specific fluorometric image acquisition and analysis procedures can be found in Ning, et al., "Imaging Fluorometer to Detect Pathological and Physiological Change in Plants," *Applied Spectroscopy*, October 1995, and in U.S. Patent Application titled Method and Apparatus for Detection Pathological and Physiological Change in Plants, filed on Oct. 29, 1996 by Ning Li, Gerald E. Edwards and Larry S. Daley, which application is incorporated herein by reference.

Spectroscopic Image Acquisition

Examples of spectroscopic image acquisition and analysis procedures are described below and can be found in Ning, et al., "Spectroscopic Imaging of Water in Living Plant Leaves—Part I," *Spectroscopy* 11 (3), March/April 1996, 34–44, and Ning, et al., "Spectroscopic Imaging of Water in Living Plant Leaves—Part II," *Spectroscopy* 11 (4), May 1996, 68–73, both of which are incorporated herein by reference.

Beer-Lambert Calculations. The Beer-Lambert law states that the intensity of radiation decreases exponentially as it passes through an absorbing medium, symbolically:

$$I = I_0 10^{-Å[J]l} \quad [1]$$

$I_0$ is the incident intensity, l is the path length through the sample of molar concentration [J] in the absorbing species J, and Å is the molar absorption coefficient (absorptivity, formerly "extinction coefficient"). The dimensionless quantity Å[J]l is called absorbance, A formerly the "optical" density (OD) of the sample, and $I/I_0$ is the transmittance, T. Since A=Å[J]l, it contains 521 a constant and l a potentially measurable length. At standardized path length, l, A is proportional to [J] or the concentration, with corrections for refractive index, and so forth. Thus, when you measure A, and you know Å and l, you can determine [J] without any reference.

EXAMPLES

The leaf of Scrofularia nodosa 'Variegata' has different hued areas of sized appropriate for in vivo calibration images from our imaging instrument with our nonimaging spectrophotometer. The plant, commonly known as knotted figwort, has variegated (multihued) oval and toothed leaves which are placed opposite each other on the stem. This plant belongs to the genus, Scrofularia L., which are Dicots found in northern temperature climates and tropical Ameria and consist of coarse foetid herbs and shrubs. Some, such as the figwort, have putative "local medical" use.

Leaf variegation in flowering plants (angiosperms) is usually a result of chloroplast mutations that segregate into different areas of tissues. This matter has some important because chloroplast function (photosynthesis) supports essentially all life on Earth. Chloroplast mutations and their complex inheritance can be investigated gated readily by in vivo spectroscopy.

"Rayleigh" scattering correction. "Rayleigh" is used herein in quotation marks, because it is defined empirically in heterogeneous living biological material by optimal fit to a $[KA]^{-4}$ correction. This putative "Rayleigh" scattering is therefore less documented than Rayleigh scattering from a defined model system where particles of known concentration and size distribution are studied in relative isolation. When measuring absorbance of in vivo or in situ samples, such leaves, scattering becomes significant. In traditional spectroscopy this is commonly corrected by using an integrating sphere. However, this cannot be done with an imaging CCD-based instrument, because each pixel of the image is collected separately.

We were able to correct this absorbance (A) data to the $R^2=0.9995$ level using two successive data treatments. The first step was $A'=\log 10\{I_{baseline}-I_{dark})/(I_{sample}-1.06*I_{dark})\}$, where 1.06 is an empirical correction that compensates for stray light characteristics of the instrument. The second step, developed empirically is $A''=(A'/1.86)*\{A'_{longest\ \lambda}+[(A'+A'_{longest\ \lambda})/A'_{longest\ \lambda}]^{-4}\}$. Fits of CCD data to integrating-sphere instrument data using other negative exponents ($\lambda^{-2}$, $\lambda^{-3}$, $\lambda^{-5}$, . . . ) yielded poorer $R^2$. Thus this second step is recognizably a "Rayleigh" correction, since experimentally, the ability to demonstrate $\lambda^{-4}$ is a good indication that Rayleigh scattering is being observed rather than absorbance, Ramon scattering, or other effects. This scattering is somewhat different from that observed by others who described their effect as the "results of macroscopic and microscopic light leaks." It is different because a CCD detector with 31,680 separate detectors reduces pattern or sieve-effects caused by unequal absorbing areas of the sample, yet retains effects of scatter phenomena.

Hazel Corylus avellana L. was chosen for these experiments, because venation in these leaves, although present, is unobtrusive except for the central vein. Thus, the visually perceptible, major, apoplastic leaf structures in the central veins of these leaves, with their light guide potential can be excluded from the tissue examined using the integrating-sphere equipped, nonimaging instrument. In subsequent imaging data, veins are readily recognizable after "Rayleigh" correction and can be evaluated separately.

Rayleigh scattering indicates that the molecules involved are smaller than the wavelengths involved. It has been suggested that this scattering is on the longer wavelength sides of absorbance maxima, but in our data we observe it on both sides of the maxima. In the range of the spectra illustrated the primary leaf chromophores are chlorophylls a and b, which are organized in chlorophyll protein complexes (CPX); CPX are inside of the chloroplast.

Chloroplast size is ~1.5×1.5 nm and the tail is ~2-nm long. Thus, chlorophylls could contribute to the "Rayleigh" scattering. Since CPX can contain <200–300 chlorophylls and have attached proteins, larger CPX are moieties comparable in size to the observed wavelength. Therefore, for CPX, one would not expect the "Rayleigh" relationship to $\lambda^{-4}$ to endure. However, because chlorophyll molecules have the appropriate absorbance, are present in large amounts (usually 0.3–3 mg/dm² of leaf surface area), and are a suitable physical size, it is rational to consider chlorophyll molecules as the most probable major source of the putative "Rayleigh" scattering observed in leaves.

Water. Water bands are broad, because thermal motion distorts the weak 0—H . . . 0 link between water molecules' absorbance. This yields a useful, if weak, maxima near 975 nm. Solvation in heavy water ($D_2$), D—0—D) water mixture in visible and very short near-IR. These spectra show that D—0—D absorbs much less in this region than water. This is significant to this use because wet and dry materials have different optical properties because of the air/water interphase. Thus, it is possible to dilute water with deuterium oxide and keep interphase signals constant. However, there are complications. A moderate peak shift when D—0—D is present in the mixture.

We calculated the spectra of H—O—D assuming completely random attachment of deuterion/hydrogen to oxygen in each solution. Then using the data at 80% v/v D—O—D/water, we assumed no absorbance for D—O—D, full absorbance for H—O—H, and we calculated the residual as H—O—D. Although this yields a lower molar absorption coefficient for the H—O bond of H—O—D than predicted by halving that of water, the H—O—D spectra explain why peak shifts occur when water is diluted with D—O—D.

This reconstructed spectra of H—O—D was used to reconstruct spectra of the other D—O—D/water solutions, then the reconstructed spectra was compared to the observed spectra. There are some slight deviations between observed and calculated spectra of mixes D—O—D and water. However, these deviations are small and thus insignificant in a biological context. Therefore, using the reconstruction method, we generated spectra for a more complete series of D—O—D/water solutions.

To test our imaging instrument we used stacks of filter paper disks wetted with D—O—D/water mixtures. There was a linear response ($R^2=0.99$) of the imaging instrument to water in disks when "Rayleigh" corrections are made. Although the linearity of this response is maintained from experiment to experiment, the response intensity varies. Factors that may contribute to variation in strength of response to water content are: (I) the water band is affected by temperature; (II) light penetration into the stacks may be difficult to control from experiment; (III) evaporation of water from the exposed paper disks may be significant; and (IV) the signal is weak.

Leaves have an external waxy cuticle that prevents water evaporation. The gas-exchange controlling apertures in this cuticle, the stomates, close when the plant is stressed by lack of water. Therefore, during experimental work, the water content of leaves, and consequently our estimate of light path through biochemically active areas, is considered constant. We use A"800 nm or A"790 nm, as reference baselines and A"970 nm as the water signal. Accumulating signals at these wavelengths is required to reduce noise. The notation A" indicates "Rayleigh" corrected attenuance.

Because the concentration of water in cells of plants is essentially constant the observed signal relates to the path of light through living cells. Thus, we investigated (using integrating sphere nonimaging spectroscopy) physically separated, uniformly hued sections from the variegated (multihued) leaf S. nodosa. Spectra were corrected for water path length. The objective was to determine whether in vivo spectroscopic signals from different portions of the leaf had chloroplasts with different CPX proportions. This is significant for theories of light shade adaptation and CPX ratio change. For horticultural purposes we also wish to determine the nature of the pigmentation variation in this possibly chimeric leafed plant, and determine whether or not areas of lower pigmentation have differently structured chloroplasts.

Chlorophyll protein complexes and water path. If the different sections of a leaf had the same proportions of CPX, we would expect to find the ratios expressed as a straight horizontal line, at a ratio of 1.0. This was not so. The lighter hued sections had proportionally more shorter-wavelength CPX, indicated by the decreased ratio we got when we divided the normalized absorbance of the darkest hued section by that of the lighter hued sections. The decrease in absorbance>690 nm is not interpreted because of the low absorbance of CPX in this area.

Fourth derivative analysis was made of the data from the different section of the S. nodosa leaf. The fourth derivative was smoothed using a Q-spline procedure which regenerates the approximate shape of the curves from point data. CPX change, here fourth-derivative analyses, show that the photosystem I (PSI) antenna signal decreases from the deepest to the lightest hued sections. Yet at the wavelengths corresponding to the light harvesting complexes (LHC) there is no perceptible decrease.

LHC commonly feeds solar energy to photosystem II (PSII)—this suggests that PSI/PSII ratios are higher in the lighter hued leaves. This is strongly consistent with the fact that the lighter hued sections are more light adapted. Because the different sections of this variegated leaf have been expose to exactly the same light conditions, we can explain this effect either as a result of self shading by the more abundant, or more pigmented, chloroplasts or as a result of selective propagation of more light adapted chloroplasts in the lighter hued sections. In addition, as chlorophyll content decreases from the deeper-pigmented, through the less-pigmented, and on to lightly pigmented areas of these S. nodosa leaves there is successively less quantum yield for photosyntheses. This suggests that what we observe is either: (I) not a true shade adaptation because we would expect greater efficiency in adapted areas; or perhaps more logically, (II) the strong light necessary for yield measurements has more permanent effects on these lightly pigmented, shade adapted areas than on those areas of the leaf that are strongly pigmented.

Path of water in situ. We investigated the path of water (Ning, et al.—Part I, FIG. 7a) in fleshy, thick, but blade-like, leaves of the genus Aloe. The inner central part of the Aloe leaf consists of huge, thin-walled, parenchyma cells with only very small intercellular air spaces. These parenchyma cells lack chloroplasts and starch. The Aloe leaves are easily sliced, transversal to the long direction, with a razor blade. The resulting sections provide a central area of parenchyma cells surrounded by a continuous band of more rigid, rind-like tissue with chloroplasts in its cells (chlorenchyma). the lack of chloroplasts, small air spaces, and thin cell walls provide a simplified and readily measurable reduced apoplast model for the optical path of water (Ning, et al.—Part I, FIG. 7a) in plant tissue. The rigid chlorenchyma of the thin sections allows us to use a micrometer to measure the thickness of the water-containing cells and compare this measurement against the spectrophotometrically (970–790 nm) measured path of water (Ning, et al.—Part I, FIG. 7c). The parenchyma of the Aloe millotii leaves we used had median, mean, and average deviation values for: (I) water content [estimated as % (FW-oven dried dry weight)/FW] of 98.7 %, 98.4%, and 0.9% of water; (II) densities relative to water at the same temperature (~23° C.) of 1.009, 1.020, and 0.022; (III) refractive indices of 1.3341, 1.3341, and 0.00026 (at 25° C., water was 1.3326). Thus because these parenchyma cells lack chloroplasts and have only small apoplastic spaces, they constitute a simplified in vivo spectroscopic model for life as bags of water.

The data in Ning, et al.—Part I, FIGS. 7a and 7c allowed us to confirm, in vivo, the correlation between 970 nm attenuance and water content. The absolute values of water absorbance were much more constant throughout different experiments than they were in experiments using paper disks saturated with deuterium oxide water mixtures. We attribute this to the cell membranes that protects the water in one A. millotii tissue from evaporation during measurement and the larger amounts of water present in these experiments. The linearity of increase of the 970–790 nm water measurement to the increased tissue thickness required did not benefit from "Rayleigh" correction in this nongreen parenchymous tissue that lacks chloroplasts and chlorophyll. this was also true for the surrounding chlorenchymous green tissues. However, this does not rule out a "Rayleigh" response to chlorophyll because highly light-conducting parenchyma is quite capable of "piping" light back into more light-scattering, rind-like chlorenchyma—it can act as a light-pipe sheath (Ning, et al.—Part I, FIG. 7c). In addition, we note that Aloe parenchymous tissues have much fewer cell walls, and thus fewer cellulose/water interactions than "Rayleigh" correctable leaf and filter paper disks.

To visualize the sudden transitions between areas of parenchyma and chlorenchyma in Aloe millotii (Ning, et al.—Part I, FIG. 7b) and between ares of high, medium, and low chlorophyll content of the variegated multihued section of leaf of S. nodosa (Ning, et al.—Part I, FIG. 7d), we summed attenuance at 10 nm intervals from 640 to 690 nm. Note the abrupt transitions in both tissues. The shades of green in the color bar indicate the intensity of chlorophyll absorbance. Yellow indicates minimal chlorophyll absorbance. In the variegated leaf of S. nodosa 'Variegate,' each colored section is relatively uniform in chlorophyll absorbance but transitions between sections are abrupt. This indicates the precision of genetic control between regions of the S. nodosa 'Variegata' leaf, as is also apparent for the two tissues of Aloe millotii. Interesting tissue development and evolutionary inferences can be deduced from these observations. Ning, et al.—Part I, FIGS. 7a and 7c point out that in plant leaves, chlorophyll content can vary abruptly.

Images of CPX relative to water path. After we were able to establish the validity of our water measurements and establish the differences in chlorophyll content between sections, we were able to use the imaging spectrometer to map the distribution of these different populations of chloroplasts in the intact leaf. FIGS. 5 describe the images obtained by different estimates of CPX and their relationships with water path. The intensity spectrum of false color is represented as a gradient of signal intensity proceeding smoothly from the blue, through the yellow, and on to the red range of the visible spectrum. A color bar clarifies this matter.

Proportions of CPX are provided in numbers determined by the equation used. Exact quantification of CPX by absorbance is imprecise because it is dependent on the relative proportions of chlorophyll a and b in the CPX, the variable size of the CPX unit, and the physiologically and biophysically variable conformation of the CPX. Molar quantification of CPX in vivo would require a physical in vivo or purification method that did not change the extinction coefficient of the CPX on in vitro extraction; such methods do not yet exists. Thus it is possible to observe changes in relative CPX proportions, but not as of yet, determine molar ratios.

Ning, et al.—Part I, FIG. 8a shows the pattern generated by our estimate of PSI [ps1=(2*A"680–A"670–A"690)/2+ A"690–A"750]. This estimates a separation of PSI signal from PSII in underivatized spectra by assuming that (I) A"670 represents a maxima for PSII with some contribution from LHC, (II) A"680 is close to the moving maxima for the antenna of PSI, and (III) that A"690–A"750 represents an essentially clean signal from the remaining portion of PSI antenna. The part of the equation 2*A"680–A"-670 –A"690 segregates from the main peak the contribution of PSII and LHC thereby generating an estimate of the contribution of PSI<690 nm. This estimate is then added to the A"690–A"750 portion of the PSI signal to generate and estimate the total PSI. Thus, Ning, et al.—Part I, FIG. 8a estimates the distribution of PSI across a portion of variegated leaf lamina. This distribution generates three major section bands that are consistent with the data from the separated sections generated by the nonimaging research spectrophotometer.

Ning, et al.—Part I, FIG. 8b shows a similar estimate of LHC. This was done by summing A"630 and A"650 maxima of chlorophyll b signals from LHC. This estimate of LHC is called Tlh and the equation is (Tlh=A"630–A"600+A"650–A"600). The pattern generated is similar to that for PSI estimate, but somewhat less distinct.

Ning, et al.—Part I, FIGS. 8c and 8d represent the data for PSI and LHC estimate corrected for water path (A"670–A"790). Water path correction generates patterns similar, but more discrete, than those generated by data uncorrected for water path. Although distributions for PSI and LHC are subtly different, these differences are not readily apparent in figures generated with these equations. Thus, Ning, et al.—Part I, FIGS. 8 do not allow ready inferences about light/shade adaptions.

To determine whether or not the chloroplasts in the distinct regions have different proportions of LHC and PSI and to then draw conclusions about light/shade adaption, we used two other equations. The first equation is an estimate of PSI/LHC ratio:[ps1/Tlh)*15+1.6]. It shows that there are at least two regions of the leaf in which dark/shade adaption of chloroplast CPX differ. In this equation, the number 15 is used to adjust contrast, and the 1.6 is adapted from the minimum chlorophyll a:b ratio naturally found in experimental data. If we check water distribution we see that water path in this leaf does not contribute to this effect. An image can also be generated by a second equation, a weighted difference spectra showing the difference between PSI (ps1) and LHC (Th1); this difference is then divided by the water path [13*(ps1–2*Tlh)/water]. The number 13 is an empirical contrast adjustment. This difference-image divides the leaf in three general sections and the distribution of these sections has no apparent relationship to the distribution of water, even when compared to an image of water path enhanced to emphasize differences Shade adaption traits revealed by this CPX analysis will relate to horticultural uses and germplasm characterization.

Operation

An instrument according to the present invention can switch between operational modes for analyzing a single plant sample both by fluorometry and spectroscopy. In a useful operating procedure, a plant sample 24 is positioned at the predetermined location 25 and its fluorescence observed by the CCD camera 33 by a procedure as described above. Next, the fluorometric light source 22 is turned off, the filter 29 is removed or rotated out of the light path, and a scan of monochromatic light from the second radiation source 42 is commenced. Transmission images are taken at successive wavelengths. Spectrophotometric and monochromator software residing in the computer 35 control the radiation source 42 and process data received by the camera 33 so that spectrophotometric images of the plant can be made at each wavelength. Transmission images are converted to the absorption format, the software then reorganizes these accumulated images to generate a spectra for each pixel. Alternatively, Fourier transform images can be acquired and used; this would reduce noise and increase speed of acquisition of images.

Although the principles of the present invention are illustrated and described with reference to preferred embodiments, it should be apparent to those of ordinary skill in the art that the illustrated embodiments may be modified in arrangement and detail without departing from such principles. The present invention includes not only the illustrated embodiments, but all such modifications, variations, and equivalents thereof as fall within the true scope and spirit of the following claims.

We claim:

1. An apparatus for analyzing radiation emitted by a sample of plant material and radiation transmitted by the sample of plant material, the apparatus comprising:

a first source of monochromatic electromagnetic radiation, which first source (a) is positioned to supply radiation incident on a sample of plant material which contains photosynthetic components, which sample is positioned at a predetermined location and (b) provides radiation of a wavelength which excites fluorescence from the sample;

a second source of monochromatic electromagnetic radiation, which second source (a) is positioned to direct radiation to pass through the sample while the sample is at the predetermined location and (b) provides radiation of a wavelength suitable for spectral imaging of the sample;

a switching mechanism for alternately supplying radiation to the sample at the predetermined location from the first and second sources of monochromatic electromagnetic radiation;

an imaging device adapted (a) to detect fluorescence which is excited from the sample by exposure to radiation from the first source while the sample is at the predetermined location, (b) to detect radiation which is transmitted through the sample from the second source while the sample is at the predetermined location, and (c) to transmit data signals that indicate the intensity of radiation detected as a function of time;

a computer which (a) is connected to the imaging device to receive the data signals that indicate the intensity of the fluorescence detected by the imaging device, (b) is programmed to note which of the data signals indicates the highest value of the fluorescence measured, and (c) is programmed then to identify information about the intensity of fluorescence that is indicated by a data signal corresponding to a fluorescence measurement which occurred at a predetermined time after the time of the noted data signal which indicated the highest value of the fluorescence; and at least one emission filter for limiting the intensity and wavelength of radiation incident on the imaging device as a result of illumination by the first source.

2. The apparatus according to claim 1 wherein the first source of monochromatic electromagnetic radiation comprises:

a light source; and at least one excitation filter for limiting the intensity and wavelength of light from the light source.

3. The apparatus according to claim 1 wherein the emission filter is movable between (a) a first position where the emission filter is in the path of radiation traveling from the sample at the predetermined location to the imaging device and (b) a second position where the emission filter is out of the path of radiation traveling from the sample at the predetermined location to the imaging device.

4. The apparatus according to claim 1 further comprising a transport mechanism for moving the apparatus or samples to place different samples at the predetermined location.

5. A method for measuring differences in plant pathology and physiology comprising:

providing an apparatus comprising a first source of electromagnetic radiation, which first source provides radiation of a wavelength which excites fluorescence from a sample of plant material containing photosynthetic components when the sample is positioned at a predetermined location, at least one excitation filter for limiting the intensity and wavelength of radiation from the first source that is incident on the sample at the predetermined location, a second source of electromagnetic radiation, which second source provides radiation of a wavelength suitable for spectral imaging of the sample and is positioned to direct radiation to pass through the sample while the sample is positioned at the predetermined location, a switching mechanism for alternately supplying radiation to the sample from the first and second sources, an imaging device positioned both (a) to detect fluorescence which is excited from the sample by exposure to radiation from the first source while the sample is at the predetermined location, and (b) to detect radiation which is transmitted through the sample from the second source while the sample is at the predetermined location, and at least one emission filter for limiting the intensity and wavelength of radiation incident on the imaging device as a result of illumination by the first source;

positioning the sample of plant material at the predetermined location;

illuminating the sample with radiation from the first source;

measuring resulting fluorescence excited from the sample as a function of time;

analyzing data obtained by the measuring to assess whether a pathological or physiological condition of the sample is abnormal; and if a pathological or physiological condition of the sample is determined to be abnormal, halting illuminating by the first source, commencing illuminating of the sample by radiation from the second source, and measuring radiation transmitted by the sample.

6. The method for measuring differences in plant pathology and physiology according to claim 5 wherein a measuring of fluorescence occurs at a predetermined time after the fluorescence has attained its maximum value.

7. The method for measuring differences in plant pathology and physiology according to claim 5 wherein the plant material is a living plant and the method further comprises:

after conducting the procedures of claim 5, positioning a second living plant at the predetermined location; and repeating the procedures of claim 5.

* * * * *